(12) United States Patent
Chapman et al.

(10) Patent No.: US 6,585,665 B1
(45) Date of Patent: Jul. 1, 2003

(54) PROBE

(75) Inventors: Derek Chapman, Norfolk (GB); Stuart Hendry, Oxfordshire (GB)

(73) Assignee: Diametrics Medical Limited, Bucks (GB)

( * ) Notice: Subject to any disclaimer, the term of this patent is extended or adjusted under 35 U.S.C. 154(b) by 0 days.

(21) Appl. No.: 09/786,277

(22) PCT Filed: Sep. 29, 1999

(86) PCT No.: PCT/GB99/03225

§ 371 (c)(1),
(2), (4) Date: Mar. 2, 2001

(87) PCT Pub. No.: WO00/20049

PCT Pub. Date: Apr. 13, 2000

(30) Foreign Application Priority Data

Oct. 2, 1998 (GB) ............................................. 9821570

(51) Int. Cl.⁷ ................................................. A61B 5/00
(52) U.S. Cl. ................. 600/581; 604/158; 128/DIG. 26
(58) Field of Search ................. 600/887, 561; 604/158, 161, 160, 159, 162, 164.13, 175; 128/DIG. 26

(56) References Cited

U.S. PATENT DOCUMENTS

| 4,245,645 | A |   | 1/1981  | Arseneault et al. |
|-----------|---|---|---------|-------------------|
| 4,306,562 | A |   | 12/1981 | Osborne           |
| 4,903,707 | A |   | 2/1990  | Knute et al.      |
| 5,104,388 | A | * | 4/1992  | Quackenbush ......... 604/164.05 |
| 5,322,513 | A | * | 6/1994  | Walker ........................ 604/161 |
| 5,891,100 | A | * | 4/1999  | Fleckenstein ................ 604/175 |
| 6,363,273 | B1| * | 3/2002  | Mastrorio et al. .......... 600/434 |

FOREIGN PATENT DOCUMENTS

| DE | 195 02 183 | 8/1996  |
| GB | 2 048 682  | 12/1980 |
| WO | 97/20530   | 6/1997  |
| WO | 98/08554   | 3/1998  |

* cited by examiner

Primary Examiner—Teresa Walberg
Assistant Examiner—Thor Campbell
(74) Attorney, Agent, or Firm—Merchant & Gould, P.C.

(57) ABSTRACT

A method of positioning a sensor in a human or animal body tissue comprising the steps of: i. providing a flexible stylet capable of penetrating the tissue, ii. providing flexible tubing having a bore capable of receiving separately the stylet and the probe; iii. positioning the stylet received in the tubing in the tissue; iv. removing the stylet; v. inserting the probe in the bore of the tubing; and vi. removing the tubing.

11 Claims, 2 Drawing Sheets

PROBE

This invention relates to a probe for insertion into the body for example for the monitoring of the body, the administration of substances or the taking of samples.

Sensors are of course well known; a good example is the Paratrend 7™ available from Diametrics Medical. This probe is primarily intended for introduction into blood vessels. Because there is little resistance the end of the sensor can be made very thin and flexible to minimise reduction to blood flow.

It may be desirable to use sensors in firmer tissue for example the brain. Difficulty may be encountered in introducing a flexible probe into such tissue.

According to an aspect of the invention there is provided a method of positioning a probe in a human or animal body tissue comprising the steps of:

i. providing a flexible stylet capable of penetrating the tissue;
 ii. providing flexible tubing having a bore capable of receiving separately the stylet and the probe;
 iii. positioning the stylet received in the tubing in the tissue;
 iv. removing the stylet;
 v. inserting probe in the bore of the tubing; and
 vi. removing the tubing.

According to the invention there is further provided apparatus for positioning and fixing a probe in human or animal body tissue comprising:

a) a flexible stylet capable of penetrating the tissue;
 b) flexible tubing having a bore capable of receiving, separately, the stylet and the probe, the probe being receivable in the flexible tubing when tubing has been positioned in the tissue, and the flexible tubing being capable of removal from the tissue following introduction of the probe.

In one embodiment, the apparatus includes means for locking the probe in position after its correct location in the body tissue.

Embodiments of the invention will be described by way of non-limiting example by reference to the accompanying figures of which:

The invention will be described by reference to introduction into the brain. Those skilled will have little difficulty in devising modifications for use in introducing probes into other areas of the body.

Adapter 1 is provided. The adapter in the illustrated embodiment is for fitment to a female luer lock 2 of a cranial bolt.

Figure 1:
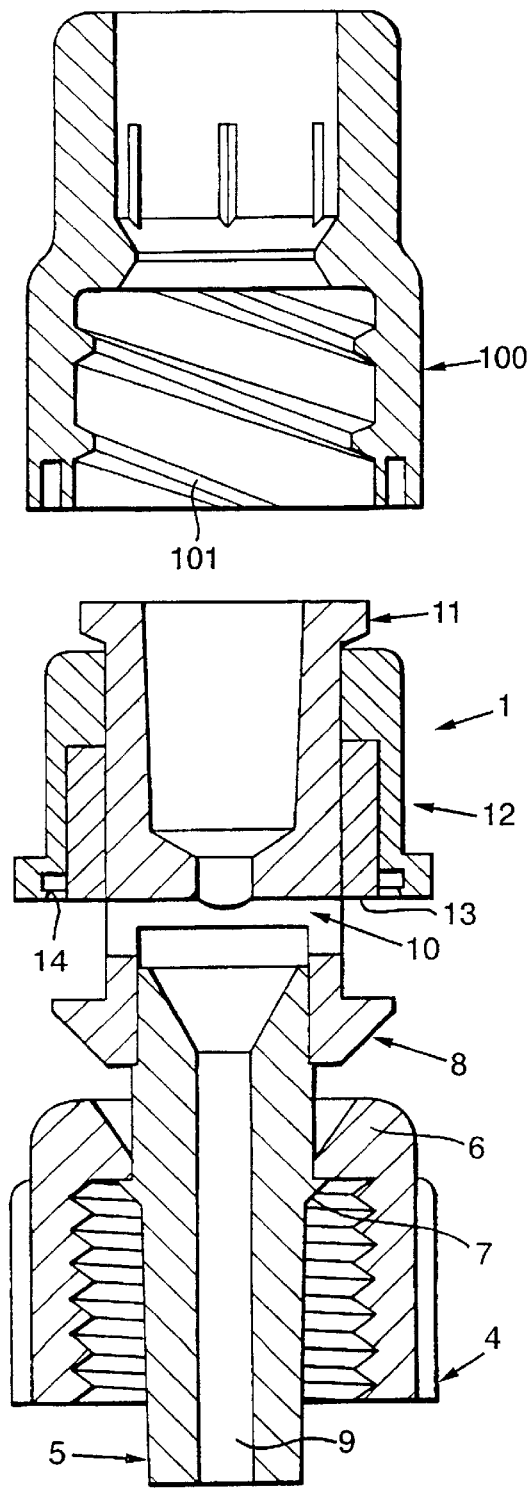
FIG. 1 is an exploded cross sectioned view of an adapter.
Figure 2:
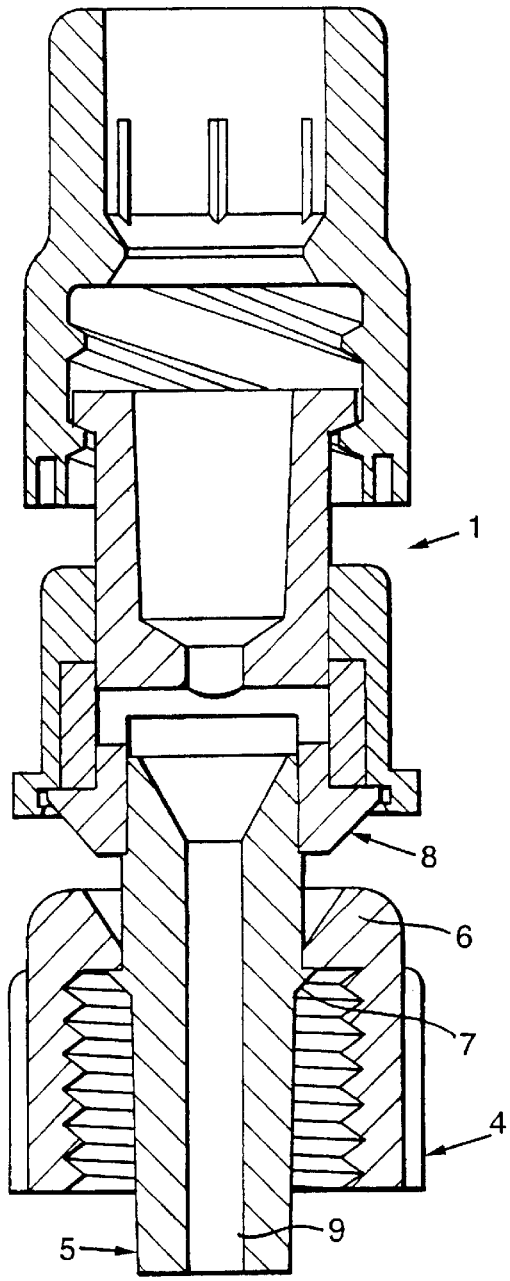
FIG. 2 is a cross sectioned view of an adapter.
Figure 3:
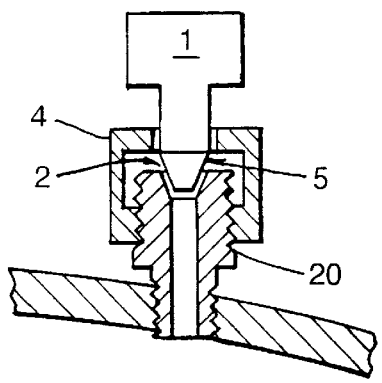
FIG. 3 is a partially cutaway view of a mounted adapter.

Adapter 1 has male luer lock 5 complementary to the female luer lock of the cranial bolt. First threaded member 6 is captive between flanges 7, 8. Threaded member 6 can, in use, engage with the cranial bolt 20. A channel 9 extends through the adapter. A cross-hole 10 is provided to allow the tubing to be removed after placement of the probe. A female luer is provided at the other end of the adapter 1 for fitment of the probe. Captive between intermediate flanges 8 and 11 is shutter 12. Flange 11 preferably is in the form of a pair of ears which as described hereinafter can function as a cam. Shutter 12 comprises a cap portion and a resilient portion 13, e.g. made from silicone rubber. The cap portion has a detent 14 engagable with the tip of flange 8. The shutter 12 is movable between the position shown in FIG. 1 and the position shown in FIG. 2. In FIG. 1 the shutter 12 is displaced away from flange 8. Cross-hole 10 is therefore open. In FIG. 2 the detent 14 has engaged the tips of flange 8. Resilient material 13 blocks the cross-hole 10 and is compressed to ensure a fluid tight seal. This arrangement means that once the probe is fitted as will be described the apparatus can be sealed preventing loss of CSF or introduction of infection.

The probe can be provided with a fastener 100. Fastener 100 is provided with a cam track 101, in the illustrated embodiment a coarse screw thread. When the probe is mounted on the adapter the fastener 100 is tightened. The fastener abuts the cap and urges it to the position shown in FIG. 2.

Flexible tubing 20 is receivable in the channel 9. Conveniently tubing 20 is made of a low friction, plastics material such as P.T.F.E. or polyethylene. Walls of tubing 20 are frangible. This may be achieved by providing one or more weakened portions 21 but the walls may be sufficiently weak inherently for this not to be necessary.

Stylet 30 is further provided. Stylet 30 should be sufficiently rigid to penetrate the tissue into which the probe is to be introduced. Typically it is a thin stainless steel wire. Desirably the stylet is sufficiently flexible for it to be manipulated into the desired position. In the illustrated embodiment the tip 31 of the stylet is more flexible than the body.

Still further there is provided a probe (not shown). The probe may be intended to measure one or more features of its surroundings. Alternatively or additionally the probe may abstract or administer materials. An example of a suitable probe is the Diametrics Neurotrend 7™ sensor.

Figure 4:
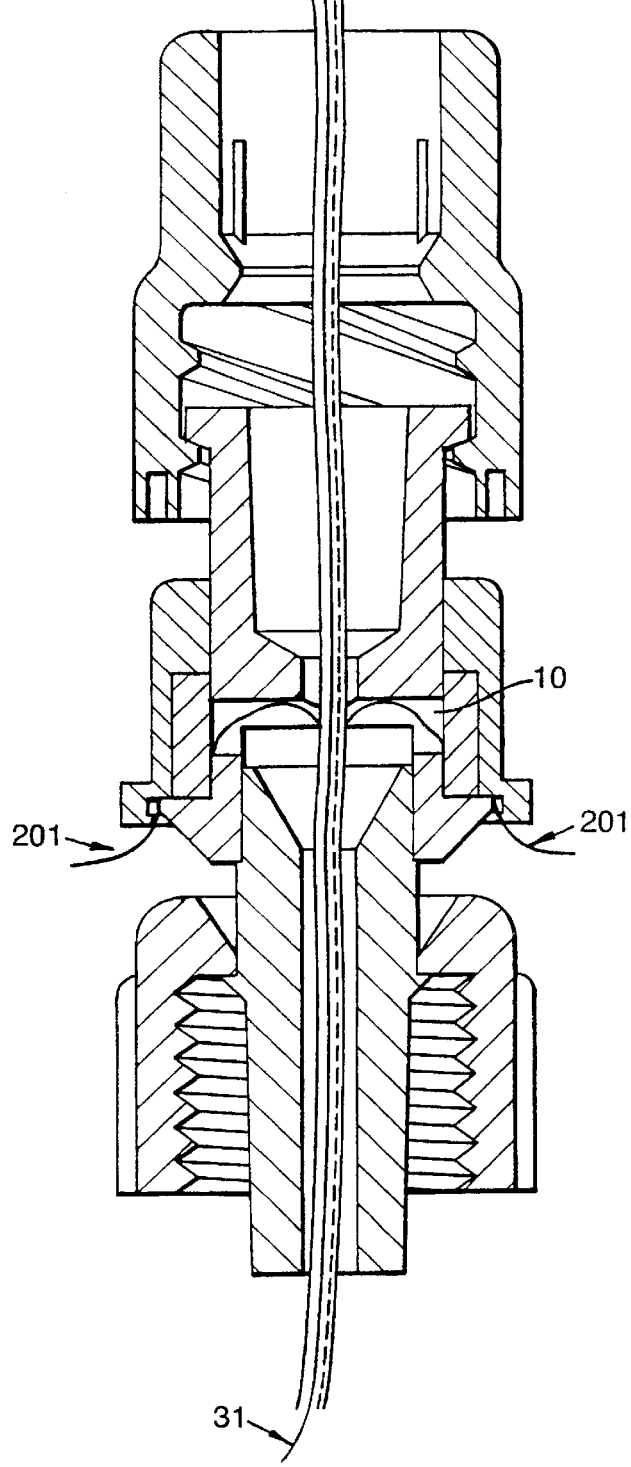
FIG. 4 is a view of the adapter of FIG. 2 with tubing and a stylet in position.

In use adapter 1 is mounted on a cranial bolt 40. The stylet 30 is passed into a flexible length of tubing 20 and the assembly inserted into a passageway previously made in the dura. The stylet is then withdrawn leaving flexible tubing 20 in position. The probe is introduced into the flexible tubing and advanced into the body to the same depth as the passageway made by the stylet, using the stylet as a depth gauge. The flexible tubing 20 prevents the tissue from bearing on the probe which would hinder its advance. Also the lubricity of the tubing permits the stylet to be removed easily and the probe slid in to take its place. When the probe is in position it is secured, e.g. by a locking member attached to the member 100. The tubing 20 is peeled away for example by tearing the frangible link and then discarded. The peelable tubing is removed by pulling it through the cross-hole 10. A fastener of the probe may then be tightened, as described above, sealing the assembly. The probe may have a tip movable relative to the body which can be advanced a further distance. In a modification, the tubing 20 may be pre-slit at is proximal end, 201 and the proximal end may project through the cross-hole 10. A fastener of the probe may then be tightened, as described above, sealing the assembly. The probe may have a tip movable relative to the body which can be advanced a further distance. In a modification, the tubing 20 may be pre-slit at its proximal end 201 and the proximal end may project through the cross-hole 10 (see FIG. 4). The peelable tubing may be removed through the cross-hole while the assembly is in the position shown in FIG. 1. However, by providing a low friction seal 13, the tubing can be drawn through the cross-hole when the assembly is fitted together as shown in FIG. 4.

The invention allows a flexible probe to be introduced into the body. The invention allows introduction of a probe with relatively little tissue damage compared to that which might occur if a large, rigid, probe where used. The invention furthermore allows probes already developed for example for introduction into veins or arteries to be employed in other areas of the body. This is advantageous since it reduces development costs and the need to keep multiple stock lines of relatively expensive probes.

What is claimed is:

1. An apparatus for positioning and fixing a probe in human or animal brain tissue;

the apparatus comprising:
    (a) a cranial bolt for fixing a probe in a desired position in brain tissue,
        (i) said cranial bolt having a passage therethrough sized to accommodate the probe;
    (b) a flexible stylet capable of penetrating the tissue; and
    (c) flexible peelable tubing having a bore dimensioned for receiving separately the stylet and the probe;
        (i) the probe being receivable in the flexible peelable tubing;
        (ii) the flexible peelable tubing being receivable in the passage in the bolt; and
        (iii) the flexible peelable tubing being capable of being peeled away while retaining the probe in place.

2. An apparatus according to claim 1 wherein:
    (a) the flexible peelable tubing has a frangible link extending the length thereof.

3. An apparatus according to claim 1 further comprising:
    (a) an adapter mounted on the cranial bolt; the adapter including means for sealing the apparatus after positioning the probe in the brain tissue.

4. An apparatus according to claim 1 wherein:
    (a) the adapter includes a hole for withdrawing the flexible tubing.

5. An apparatus according to claim 4 wherein:
    (a) the adapter includes a shutter moveable between a first position in which the hole is open and a second position in which the hole is closed by the shutter.

6. An apparatus according to claim 5 wherein:
    (a) the shutter comprises a resilient portion oriented to block the hole and provide a fluid tight seal when the shutter is in the second position.

7. An apparatus according to claim 4 wherein:
    (a) the adapter includes a flange; and
    (b) the shutter comprises detents arranged to engage the flange on the adapter when the shutter is in the second position, and lock the shutter in the second position.

8. An apparatus according to claim 5 further comprising:
    (a) a screw-threaded member turnable to urge the shutter from the first position to the second position.

9. A method of positioning and fixing a probe in brain tissue of a human or animal comprising steps of:
    (i) fixing a cranial bolt into a hole in a skull of the human or animal body;
    (ii) providing a flexible stylet capable of penetrating the brain tissue;
    (iii) providing a flexible tubing having a bore capable of receiving separately the stylet and the probe;
    (iv) positioning the stylet in the tubing and passing the stylet and tubing through a passage in the cranial bolt and into the brain tissue;
    (v) removing the stylet while retaining the tubing in the brain tissue;
    (vi) using the stylet as a depth gauge, inserting the probe into the tubing; and
    (vii) peeling away the tubing while retaining the probe in place.

10. A method as claimed in claim 9 wherein:
    (i) said step of peeling away the tubing while retaining the probe in place includes retaining the probe in place using an adapter attached to the cranial bolt.

11. A method as claimed in claim 10 further comprising:
    (i) providing a seal for the adapter to prevent loss of CSF or introduction of infection after peeling away the tubing.

* * * * *